(12) United States Patent
Buffington et al.

(10) Patent No.: US 8,309,931 B2
(45) Date of Patent: Nov. 13, 2012

(54) RAPID DIAGNOSIS OF A DISEASE CONDITION USING INFRARED SPECTROSCOPY

(75) Inventors: Charles A. Buffington, Worthington, OH (US); Daniel Emilio Rubio-Diaz, Spring Lake, MI (US); Luis E. Rodriguez-Saona, Dublin, OH (US); Judi L. Stella, Carroll, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 12/933,960

(22) PCT Filed: Mar. 30, 2009

(86) PCT No.: PCT/US2009/038771
§ 371 (c)(1),
(2), (4) Date: Dec. 15, 2010

(87) PCT Pub. No.: WO2009/121054
PCT Pub. Date: Oct. 1, 2009

(65) Prior Publication Data
US 2011/0168897 A1    Jul. 14, 2011

Related U.S. Application Data

(60) Provisional application No. 61/040,627, filed on Mar. 28, 2008.

(51) Int. Cl.
*G01J 5/02* (2006.01)
(52) U.S. Cl. .................................................. 250/341.8
(58) Field of Classification Search .................. 250/340, 250/341.1–341.8
See application file for complete search history.

(56) References Cited

U.S. PATENT DOCUMENTS

| | | | |
|---|---|---|---|
| 5,473,160 A | 12/1995 | Eysel et al. | |
| 6,270,986 B1 | 8/2001 | Wong | |
| 6,331,395 B1* | 12/2001 | Burchell et al. | 435/6.11 |
| 6,620,621 B1 | 9/2003 | Cohenford et al. | |
| 6,793,624 B2 | 9/2004 | Tsenkova | |
| 2002/0027649 A1* | 3/2002 | Chudner | 356/39 |
| 2002/0164810 A1* | 11/2002 | Dukor et al. | 436/64 |
| 2003/0122081 A1* | 7/2003 | Herrera et al. | 250/341.6 |
| 2004/0253575 A1 | 12/2004 | Manfait et al. | |
| 2005/0048527 A1* | 3/2005 | Allawi et al. | 435/6 |
| 2008/0261258 A1* | 10/2008 | Smith et al. | 435/29 |
| 2008/0285122 A1 | 11/2008 | Hoult et al. | |
| 2009/0040517 A1 | 2/2009 | Maier et al. | |

(Continued)

OTHER PUBLICATIONS

Aaron, L.A. et al, Overlapping Conditions Among Patients With Chronic Fatigue Syndrome, Fibromyalgia, and Temporomandibular Disorder, Arch Intern Med, Jan. 24, 2000, pp. 221-227, 160.

(Continued)

*Primary Examiner* — Kiho Kim
(74) *Attorney, Agent, or Firm* — Ballard Spahr LLP (57) ABSTRACT

Reliable and rapid diagnostic methods for many functional syndromes (FS) such as Bladder Pain Syndrome/Interstitial Cystitis (IC) are not available. Exemplary embodiments include rapid and accurate methods for diagnosing FS in humans and domestic cats using infrared microspectroscopy (IRMS). Exemplary methods utilize Soft Independent Modeling by Class Analogy (SIMCA) to create classification models. Exemplary methods utilize classification models to classify a test subject's condition (e.g., healthy/sick). Using these classification models, various embodiments enable diagnosis based on spectra data from a fluid biomedical specimen. Exemplary embodiments may be useful to rapidly diagnose IC and various other conditions in humans, cats, and/or other mammals.

17 Claims, 5 Drawing Sheets

U.S. PATENT DOCUMENTS

2010/0034874 A1* 2/2010 Hirai et al. ............... 424/450

OTHER PUBLICATIONS

Aaron, L.A. et al., Comorbid Clinical Conditions in Chronic Fatigue, Journal of General Internal Medicine, Jan. 2001, pp. 24-31, 16.
Badawy, A.A-B. et al., Heterogeneity of serum tryptophan concentration and availability to the brain in patients with the chronic fatigue syndrome, Journal of Psychopharmacology, 2005, pp. 385-391, 19(4).
Bellmann-Weiler, R. et al., IFN-gamma mediated pathways in patients with fatigue and chronic active Epstein Barr virus-infection, Journal of Affective Disorders, 2008, pp. 171-176, 108.
Bogart, L.M. et al., Symptoms of Interstitial Cystitis, Painful Bladder Syndrome and Similar Diseases in Women: A Systematic Review, The Journal of Urology, Feb. 2007, pp. 450-456, 177.
Buffington, C.A.T. et al., Idiopathic Cystitis in Cats: An Animal Model of Interstitial Cystitis, Interstitial Cystitis, 1997, pp. 25-31, Chapter 4, Lippincott-Raven, Philadelphia.
Buffington, C.A.T. et al., Feline interstitial cystitis, J. Am. Vet. Med. Assoc., Sep. 1, 1999, pp. 682-687, 215(5).
Buffington, C.A.T., Comorbidity of Interstitial Cystitis With Other Unexplained Clinical Conditions, The Journal of Urology, Oct. 2004, pp. 1242-1248, 172.
Buffington, C.A.T., Developmental Influences on Medically Unexplained Symptoms, Psychotherapy and Psychosomatics, 2008, pp. 1-6, 130.
Carmona, P. et al, In vivo detection of scrapie cases from blood by infrared spectroscopy, Journal of General Virology, 2005, pp. 3425-3431, 86.
Clauw, D.J. et al, Chronic Pain and Fatigue Syndromes: Overlapping Clinical and Neuroendocrine Features and Potential Pathogenic Mechanisms, NeuroImmunoModulation, 1997, pp. 134-153, 4.
Coomans, D. et al., Use of a Microcomputer for the Definition of Multivariate Confidence Regions in Medical Diagnosis Based on Clinical Laboratory Profiles, Computers and Biomedical Research, 1984, pp. 1-14, 17.
Curhan, G.C. et al., Epidemiology of Interstitial Cystitis: A Population Based Study, The Journal of Urology, Feb. 1999, pp. 549-552, 161.
Dantzer, R. et al., From inflammation to sickness and depression: when the immune system subjugates the brain, Nature Reviews Neuroscience, Jan. 2008, pp. 46-56, 9.
Diessel, E. et al., Nanoliter Serum Sample Analysis by Mid-infrared Spectroscopy for Minimally Invasive Blood-Glucose Monitoring, Applied Spectroscopy, Nov. 4, 2005, pp. 442-451, 59(4).
Dimitrakov, J. et al., Adrenocortical Hormone Abnormalities in Men with Chronic Prostatitis/Chronic Pelvic Pain Syndrome, Urology, 2008, pp. 261-266, 71(2).
Ellis, D.I. et al., Metabolic Fingerprinting With Fourier Transform Infrared Spectroscopy, Metabolic Profiling: Its Role in Biomarker Discovery and Gene Function Analysis, 2003, Chapter 7, Kluwer Academic Publishers, Dordrecht.
Erickson, D.R. et al., A Comparison of Multiple Urine Markers for Interstitial Cystitis, The Journal of Urology, Jun. 2002, pp. 2461-2469, 167.
Fabian, H. et al., Diagnosing benign and malignant lesions in breast tissue sections by using IR-mictrospectroscopy, Biochimica et Biophysica Acta, 2006, pp. 874-882, 1758.
Gunnar, M.R. et al., Bringing basic research on early experience and stress neurobiology to bear on preventive interventions for neglected and maltreated children, Development and Psychopathology, 2006, pp. 651-677, 18.
Hewitt, S.M. et al., Discovery of Protein Biomarkers for Renal Diseases, Journal of the American Society of Nephrology, 2004, pp. 1677-1689, 15.
Hsieh, T-F. et al, Possible application of Raman microscpectroscopy to verify the interstitial cystitis diagnosis after potassium sensitivity test: Phenylalanine or tryptophan as a biomarker, Disease Markers, 2007, pp. 147-152, 23.
Kaufman, D.M. et al., Interstitial Cystitis (IC) Overview, Incidence of IC, 3 pages, Jun. 10, 1998, web pages accessed at http://www.urologychannel.com/interstitialcystitis/index.shtml.
Kroenke, K., Studying Symptoms: Sampling and Measurement Issues, Annals of Internal Medicine, May 1, 2001, pp. 844-853, 134(9).
Kvalheim, O.M. et al., SIMCA—Classification by Means of Disjoint Cross Validated Principal Components Models, Multivariate Pattern Recognition in Chemometrics 1992, pp. 209-248, Chapter 7, Elsevier, The Netherlands.
Lambert, J. et al., Introduction, Organic Structural Spectroscopy, 1998, pp. 1-6, Chapter 1, Prentice Hall, Upper Saddle River, New Jersey.
Liu, K-Z. T. Al.., Molecular and chemical characterization of blood cells by infrared spectroscopy: A new optical tool in hematology, Blood Cells, 2005, pp. 404-412, 35.
Liu, Z. et. al., Plasma Level of Tryptophan in Patients With Chronic Fatigue Syndrome, Journal of Neurochemistry, 2007, pp. 115-116, 102(Suppl.1).
Merrell, K. et al., Analysis of Low-Abundance Serum Proteins Using Mass Spectrometry, Journal of Biomolecular Techniques, Mar. 2004, p. 23, 15(1).
Metts, J.F. et al., Interstitial Cystitis: Urgency and Frequency Syndrome, American Family Physician, Oct. 1, 2001, pp. 1199-1206, 64(7).
Naumann, D., FT-Infrared and FT-Raman Spectroscopy in Biomedical Research, Infrared and Raman Spectroscopy of Biological Materials, 2000, pp. 323-380, Chapter 9, Marcel Dekker, New York.
Naumann, D., FT-Infrared and FT-Raman Spectroscopy in Biomedical Research, Applied Spectroscopy Reviews, 2001, pp. 239-298, 36(2&3).
Nigro, D.A. et al., Interstitial Cystitis: Clinical and Endoscopic Features, Interstitial Cystitis, 1997, pp. 137-142, Lippincott-Raven, Philadelphia.
Payne, C.K. et al., Interstitial Cystitis and Painful Bladder Syndrome, The Journal of Urology, Jun. 2007, pp. 2042-4049, 177.
Petrich, W. et al., Disease pattern recognition in infrared spectra of human sera with diabetes mellitus as an example, Applied Optics, Jul. 1, 2000, pp. 3372-3379, 39(19).
Petrich, W., Mid-Infrared and Raman Spectroscopy for Medical Diagnostics, Applied Spectroscopy Reviews, 2001, pp. 181-237, 36(2&3).
Pike Technologies, ATR—Theory and Applications, 2005, 3 pages, Pike Technologies, Madison, Wisconsin.
Ratner, V. et al., Re: Epidemiology of Interstitial Cystitis: A Population Based Study, The Journal of Urology, Letters to the Editor, Aug. 1999, p. 500, 162.
Sakudo, A. et al., Spectroscopic diagnosis of chronic fatigue syndrome by visible and near-infrared spectroscopy in serum samples, Biochemical and Biophysical Research Communications, 2006, pp. 1513-1516, 345.
Tirumalai, R.S. et al., Characterization of the Low Molecular Weight Human Serum Proteome, Molecular & Cellular Proteomics, 2003, pp. 1096-1103, 2.10.
Westropp, J.L. et al., Evaluation of the effects of stress in cats with idiopathic cystitis, American Journal of Veterinary Research, Apr. 2006, pp. 731-736, 67(4).
Westropp, J.L. et al., In Vivo Models of Interstitial Cystitis, The Journal of Urology, Feb. 2002, pp. 694-702, 167.
Yunus, M.B., Central Sensitivity Syndromes: A New Paradigm and Group Nosology for Fibromyalgia and Overlapping Conditions, and the Related Issue of Disease versus Illness, Semin Arthritis Rheum, 2008, pp. 339-352, 37.

* cited by examiner

RAPID DIAGNOSIS OF A DISEASE CONDITION USING INFRARED SPECTROSCOPY

CROSS-REFERENCE TO RELATED APPLICATIONS

This non-provisional application claims the benefit of priority from U.S. Provisional Patent Application No. 61/040,627, filed Mar. 28, 2008, which is hereby incorporated by reference in its entirety.

TECHNICAL FIELD

The present invention relates to methods for diagnosing disease conditions in a patient, particularly rapid diagnostic methods using multivariate classification models.

BACKGROUND OF THE ART

Functional syndromes (FS) are illnesses characterized by constellations of symptoms, suffering, and disability that cannot be explained by an evidence-based pathophysiologic mechanism. Functional syndromes, such as chronic fatigue syndrome, fibromyalgia, interstitial cystitis (IC), and irritable bowel syndrome are among the most common reasons human beings seek medical care. Physicians generally adopt a symptomatic empirical approach for these conditions. They are important causes of chronic illness and healthcare utilization, because patients often do not get better as a result of currently available therapies.

Patients with FS are seen by all medical specialties. IC is one of the most common FS in urology. IC is characterized by chronic pain, excessive urgency and frequency of urination, nocturia, and negative urine cultures. As many as 750,000 women in the United States may suffer from IC. Data from the Nurses' Health Study suggests that the prevalence of IC among women is about 52-67 per 100,000. Patients often reach a diagnosis of IC through an emotionally charged and difficult route, the product of numerous physician encounters and stigmatizing experiences. IC interferes with employment, social relationships and sexual activity. The chronic pain, frequency, urgency and sleep deprivation associated with IC may contribute to psychological stress and secondary depression. Chronic bladder and pelvic pain is usually moderate to severe in patients with IC; more than one half of symptomatic patients also suffer from depression, and suicidal ideation is 3-4 times more common in these patients than in the general population.

Diagnosing FS is difficult. One of the reasons for this is that there may be a variety of nonspecific symptoms associated with the FS. Before a diagnosis of IC can be made, for example, many non-related conditions and disorders (urinary tract infections, vaginal infections (in women), chronic prostatitis (in men), bladder cancer, bladder inflammation or infection, kidney stones, endometriosis, neurological disorders, sexually transmitted diseases among other) must be ruled out. Currently there is no well accepted diagnostic test for many functional syndromes like IC. It is therefore an unmet advantage of the prior art to provide a simple, rapid, and reliable method to diagnose functional disorders such as IC. A similar syndrome, called feline IC (FIC), is the most common lower urinary tract disorder of domestic cats.

SUMMARY OF THE INVENTION

This and other unmet advantages are provided by disclosed methods described and shown in more detail below.

Various embodiments combine infrared microspectroscopy (IRMS) with the power of multivariate statistical approaches such as principal components analysis (PCA) in methods useful for rapid and reliable clinical diagnostic analyses. Exemplary embodiments utilizing multivariate classification models may be used for the rapid diagnosis of IC and other disorders from serum or other fluid biomedical specimens.

Exemplary embodiments provide methods for rapidly diagnosing specific disease conditions such as IC and other functional syndromes. At least one embodiment comprises a method for diagnosing a disease condition, comprising: receiving a fluid biomedical specimen from a test subject; separating the specimen to obtain a desired fraction; depositing an aliquot of the desired fraction onto a slide; drying the aliquot; collecting infrared spectral data from the aliquot; and identifying a test subject's condition by analyzing the infrared spectra data using multivariate classification models.

In various embodiments, the specimen may be diluted to form a specimen-water solution prior to separating the specimen. In some embodiments, the separating step may include the step of filtering the specimen with a membrane. The separating step may include the step of centrifuging the specimen using a centrifugal filter device.

In an exemplary embodiment, multivariate classification models may be developed based on a principle components analysis using previously provided spectra from afflicted and non-afflicted subject populations. In an alternative embodiment, the multivariate classification models may be downloaded from a reference database.

In at least one embodiment the drying step further includes the step of forming a dried film on the slide; and the collecting step comprises obtaining infrared spectral data from a preselected region of the dried film. In a preferred embodiment, at least two spectra collection regions are substantially equidistant from the center of the dried film.

Although various embodiments utilized dried films for the collection of IR spectra information, the infrared spectral data in the collecting step may alternatively be obtained via an attenuated total reflectance Fourier transform (FT)-IR method. In this case, the need for diluting the sample or the creation of dried films may be obviated.

Exemplary methods presented herein may assist the clinician by providing a rapid and reliable means for diagnosing functional syndromes like IC after receiving no more than a fluid biomedical specimen from the patient.

BRIEF DESCRIPTION OF THE DRAWINGS

A better understanding of the embodiments will be obtained from a reading of the following detailed description and the accompanying drawings in which.

(C) Cooman's plot of cat serum samples after membrane filtration, which increased the distance (difference) between the groups.

DETAILED DESCRIPTION OF A PREFERRED EMBODIMENT

Vibrational spectroscopic methods such as Raman and FT-IR spectroscopy are emerging as powerful techniques in biomedicine. IR spectroscopy is a well established analytical technique for rapid, high-throughput, non-destructive analysis of a wide range of sample types based on the principle that chemical structures in biological samples absorb particular frequencies of infrared light. The IR absorption spectrum provides a characteristic "fingerprint" of substances such as lipids, proteins, nucleic acids, polysaccharides, and phosphate-carrying compounds present in the sample. The resulting infrared absorption spectrum provides information concerning the biochemistry of biological fluids and tissues, and has the ability to detect biochemical changes caused by pathologies, even at very early stages of the disease.

In IR microspectroscopy the IR spectrum is collected from a particular area of the sample by using an integrated microscope; this technique offers the possibility to associate IR spectra with specific structures in the specimen.

At least one exemplary embodiment includes the following steps:
1. Prepare a solution using the patient's serum and distilled water.
2. Use separation techniques, such as ultrafiltration, to fractionate serum constituents.
3. Prepare a dried serum film (DSF) on a microscope slide by vacuum drying 0.5-1.0 µl of the solution fraction from step 2.
4. Collect IR spectra from the DSF.
5. Use established statistical methods to diagnose the subject condition using the DSF IR spectral information.

In an alternative embodiment, Attenuated Total Reflectance (ATR) techniques can be used (described below) which may obviate the need to dilute the specimen or produce a film. In such a case, the fluid specimen can be deposited directly and subsequently analyzed. The sample is then brought into direct contact with a crystal (internal reflection element, IRE) that has a much higher refractive index than that of the sample. When the angle of incidence of the light from the IRE to the sample exceeds the crystal angle, total internal reflection takes place. When this total internal reflection takes place, the light penetrates slightly into the sample producing an absorbance-like spectrum.

EXAMPLES

The following examples demonstrate various techniques and procedures useful for the exemplary embodiments. Although embodiments disclosed herein use serum as the fluid biomedical specimen, one skilled in the art will appreciate that many different fluid biomedical specimens (e.g., urine, semen, saliva, etc) may be analyzed according to exemplary methods of the various embodiments described below. Furthermore, although embodiments demonstrated herein relate primarily to IC, the invention is not so limited. Because many disease states lead to changes in the chemical composition of biomedical fluids like serum, embodiments of the present invention may be broadly applicable for the diagnosis of many disease conditions.

Example 1

Collection of Fluid Biomedical Specimens

Cat Specimens: frozen serum samples from 34 domestic cats (*Felis silvestris catus*) were provided by the Department of Veterinary Clinical Sciences of The Ohio State University (OSU) and diagnosed by Dr. Tony Buffington based on a complete physical diagnosis and the pertinent NIDDK inclusion and exclusion criteria. 22 samples came from cats with FIC and 12 from healthy cats (18 female and 16 male). Samples were stored at −40° C. in the Food Science Department of the OSU.

Human Specimens: 30 frozen samples of human serum from the Harvard Urological Diseases Center (Boston, Mass.) were received and stored at −40° C. in the Food Science Department of The Ohio State University. 18 from these samples belonged to IC patients and 12 to healthy subjects; 15 were from female and 15 were from male individuals. One human sample was removed from the study because of the presence of small particles and atypical dried film formation. The IC patients satisfied the criteria for the diagnosis of IC described by the NIDDK.

Example 2

Preparation of IR-Films

Dried Serum Films (DSF)

Serum was separated by centrifugation and samples were immediately stored at −20° C. to maintain their integrity until analysis. Two types of DSF were prepared using 1:1 serum/water solutions. The first type of films (type a) was prepared with human and cat sera by vacuum drying (~4 minutes) 0.5 µl of the serum solution over high infrared reflectance microscope slides (circular area of 3.8 mm$^2$). The second type of DSF (β) was prepared by ultrafiltering the serum solution through a cellulose membrane of 10,000 nominal molecular weight limit (NMWL) at 16,000×g for 10 min using a microcentrifuge (Model 5415R, Eppendorf, Westbury, N.Y.).

For α and β DSF, an aliquot (0.5-1 µl) of the filtrate was placed onto SpectCONC-IR or SpectRIM (Tienta Sciences, IN) microscope slides (circular area of 3.8 mm$^2$) and dried at room temperature under vacuum to produce dried serum films (DSF). (DSF type β was evaluated only with cat samples). IR spectra collected from the DSF were used to create classification models using Soft Independent Modeling by Class Analogy (SIMCA) (details below).

Figure 1:
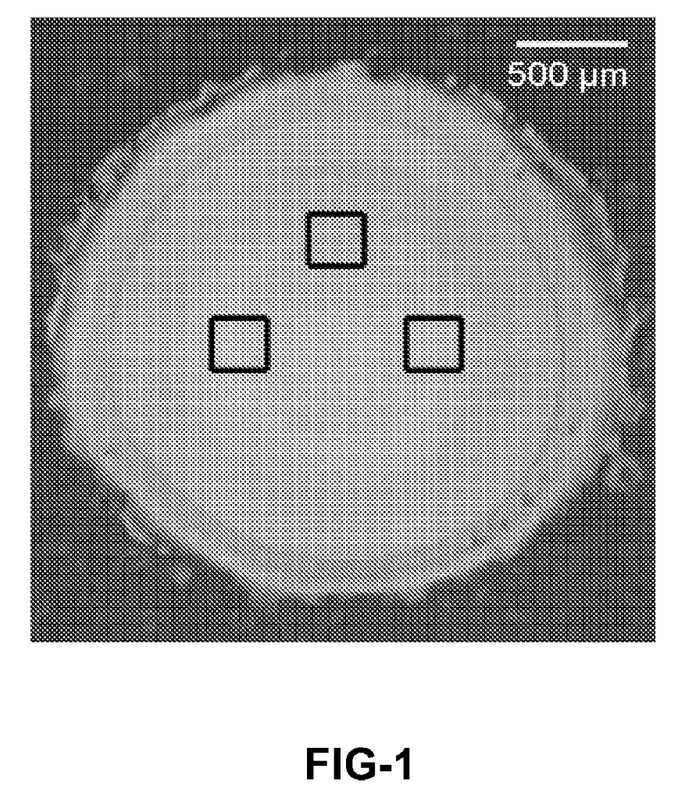
FIG. 1 shows a dried film of an exemplary embodiment. Squares show typical regions where spectra may be collected.

The preparation of DSF was found to impact the reproducibility of the IR measurements. FIG. 1 shows a microscope picture of a cat DSF (CDSF). Three regions were selected for spectra collection. (FIG. 1). Three main factors influenced the structure of DSFs: the concentration of the serum solution, the volume of sample to dry (given a specific drying area) and the drying time. Although a much wider range of concentrations may be appropriate for any given application, a 1:1 to 1:5 solution of serum in distillated water yielded acceptable IR spectra data for these examples. These solutions allowed for low sample volumes per film (0.5-1.0 µl), high infrared absorbance, and short drying times (~4 min). For a given application, the aliquot may comprise as little as 0.01 µl to 1 ml of the desired fraction. Collecting spectra from DSF areas with similar appearance, roughly equidistant to the center of the film, increased the reproducibility of the protocol.

Example 3

IR Spectra Collection

IR spectra were collected using an FT-IR microscope (UMA 600 series IR microscope interfaced with a FTS Excalibur 3500 GX FTIR spectrometer; Varian, Calif.) equipped with a broadband mercury-cadmium-telluride detector. Each spectrum was obtained from a 0.0625 mm2 square area with a frequency range of 4000 to 700 $cm^{-1}$ by co-adding 128 scans at a resolution of 8 $cm^{-1}$. Immediately after vacuum drying the serum solution 3 spectra from different regions roughly equidistant to the center were collected from every film. Two films were prepared from each serum solution; thus, a total of 6 spectra were gathered per sample.

Figure 2:
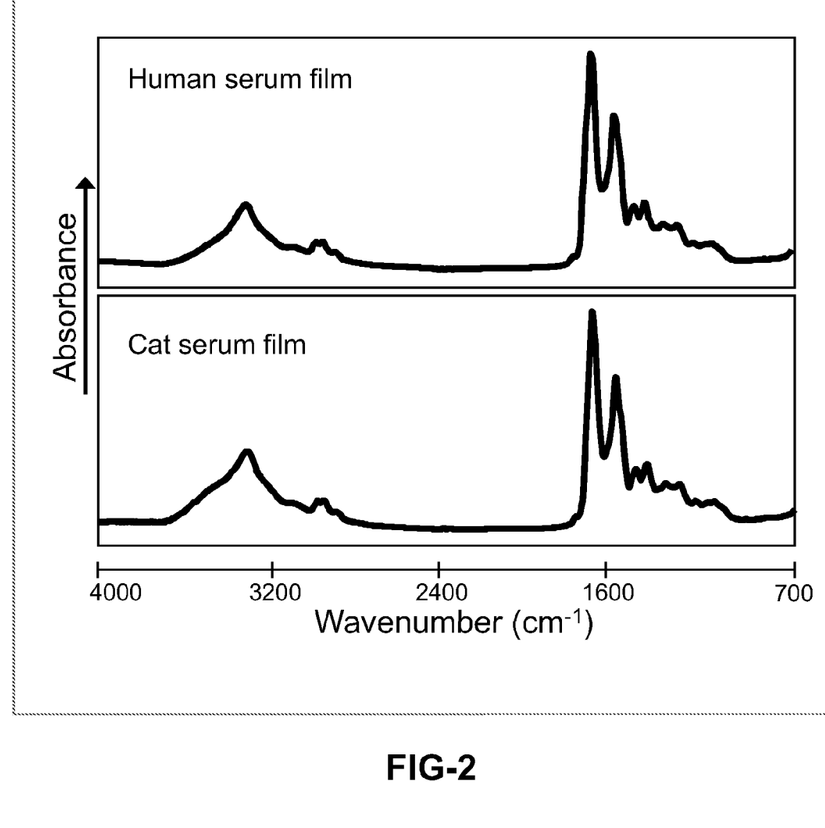
FIG. 2 shows typical reflectance infrared microspectroscopy spectrum of human and domestic cat serum films collected in the 4000-700 $cm^{-1}$ region.

FIG. 2 shows typical reflectance infrared microspectroscopy spectrum of human and domestic cat serum films collected in the 4000-700 $cm^{-1}$ region. Infrared spectra from feline (FSF) and human serum films (HSF) showed similar spectral profiles (FIG. 2). Although no observable differences between spectra from (F)IC affected and healthy subjects (not shown) were apparent, dissimilarities were detected after mathematical transformations (normalization, second derivative) and multivariate analysis.

Figure 3:
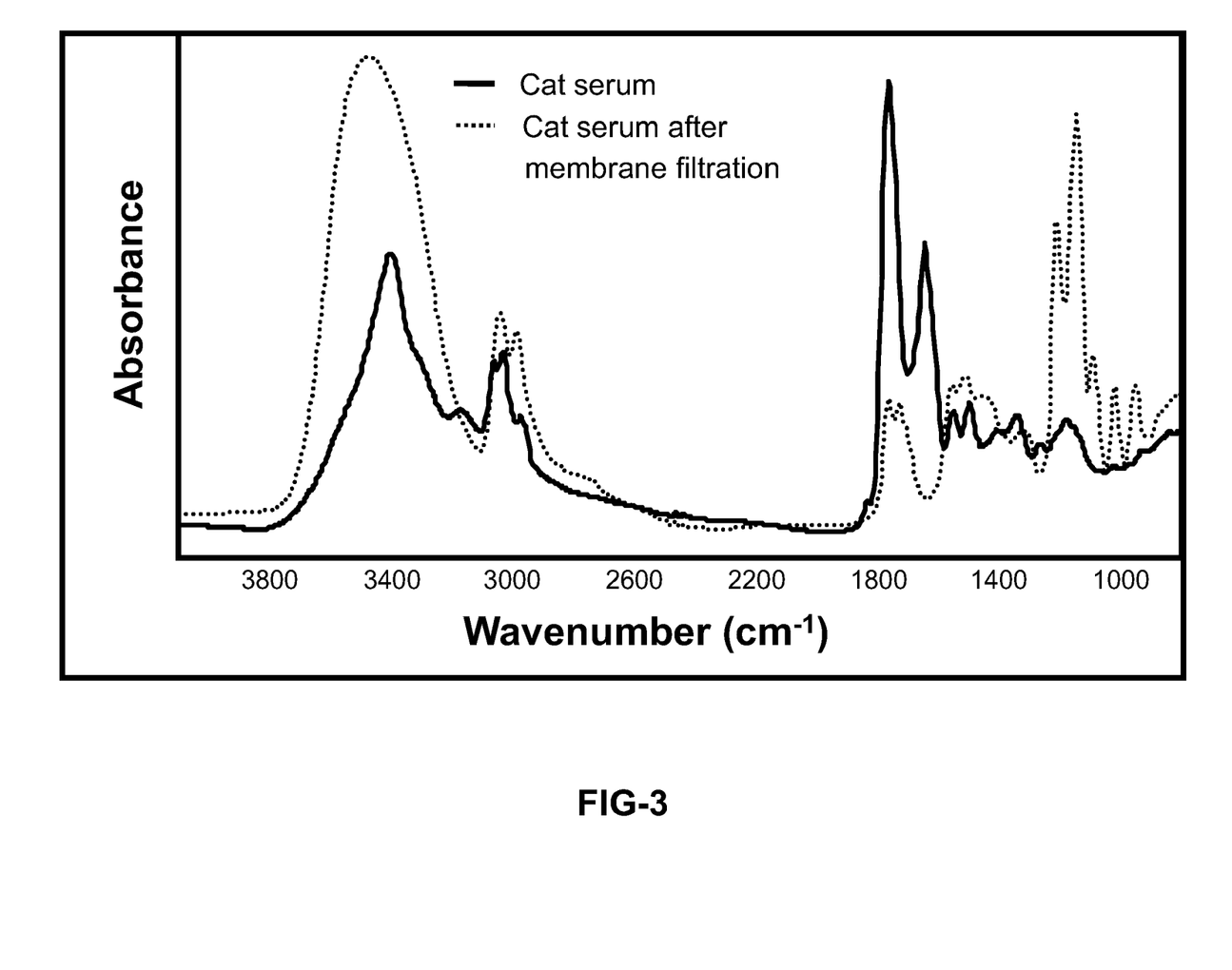
FIG. 3 shows infrared microspectroscopy spectra of cat serum sample before and after membrane filtration.

Most serum protein (60-80 mg/mL) are large (65-97% is serum albumin and immunoglobulins); however, biomarkers often are low-molecular-weight proteins or peptides secreted into the bloodstream as a result of a disease process. To reduce interferences caused by large molecules that may not be related to IC, films were prepared after ultrafiltration of cat serum solutions using a 10,000 molecular weight cut-off membrane (DSF β). Differences in IR spectral features between films prepared with or without the ultrafiltration step were evident (FIG. 3), with a marked decrease in some IR absorption bands in the 1400-1800 $cm^{-1}$ region, probably due to the removal of large proteins.

As a prophetic alternative to collecting spectra data from dried films, various embodiments may employ Attenuated Total Reflectance (ATR) techniques to obtain the spectra information. See e.g., United States Patent Application 20080285122, hereby incorporated by reference in its entirety. ATR is a technique used in spectroscopy, such as FT-IR spectroscopy, to obtain spectral measurements from samples that are difficult to analyze by other means such as transmission or reflection.

This technique relies on total internal reflection. The sample is placed proximately into direct contact with a crystal (known as an internal reflection element, IRE). The crystal has a refractive index that is much higher than that of the sample. When the angle of incidence of the light from the IRE to the sample exceeds the crystal angle, total internal reflection takes place. When this total internal reflection occurs, the light penetrates slightly into the sample producing an absorbance-like spectrum.

Typically apparatus for carrying out ATR measurements will comprise a spectrometer to provide wavelength discrimination, an illumination system for directing light onto a sample, an ATR optic which provides a sample plane and a collecting/detecting system to capture light that has interacted with the sample.

The ATR optic is arranged in such a way as to reflect all incident light from a designated sample plane by means of the phenomenon of total internal reflection. Spectral information concerning the sample is derived from the interaction of the sample with an evanescent electric field that exists immediately outside the reflecting surface. The absorption of energy from this field attenuates the reflection and impresses spectral information on the light beam.

An imaging ATR system can be constructed based upon these principles by arranging to illuminate an area of a sample and by arranging the collecting system to have imaging properties. Light returning from spatially distinct regions of the sample is collected on a detector or a detector array such as a one dimensional or two dimensional array of detectors; spectral information thus collected can be compiled into a spectral image of sample.

An imaging ATR system can be constructed in the form of a reflectance microscope. In such an arrangement light is directed onto and collected from a reflective sample by means of an imaging optic. An ATR optic for such a system can conveniently comprise a hemispherical plano-convex lens made of a high refractive index material such as germanium. The optic is arranged so that the convex spherical surface is directed towards the microscope optic with its centre of curvature arranged to be coincident with the focal plane of the imaging system. The sample is presented to the flat surface of the ATR.

The microscope includes a moveable stage which has associated motors for moving the stage in x, y and z directions under processor control. Imaging is carried out using a small linear array detector and physically moving the stage and therefore the crystal/sample combination laterally relative to the optical axis of the microscope. As the stage is moved images can be collected by the detector from different parts of the sample and in this way a spatial image can be accumulated.

ATR generally allows qualitative or quantitative analysis of samples with little or no sample preparation, which greatly speeds sample analysis. The main benefit of ATR sampling comes from the very thin sampling path length and depth of penetration of the IR beam into the sample. This is in contrast to traditional FT-IR sampling by transmission where the sample usually is diluted with an IR transparent salt and pressed into a pellet or a thin film prior to analysis to prevent totally absorbing bands in the IR spectrum.

Example 4

Creation of Classification Models

Classification Models

Spectral differences between samples from subjects with (F)IC, subjects with other medical disorders, and asymptomatic controls were evaluated using multivariate statistical techniques to resolve spectral information of interest and to cluster the samples according to the presence of the disease. Soft Independent Modeling Class Analogy (SIMCA) was carried out using Pirouette pattern recognition software (V 3.02 for Windows NT, Infometrix, Inc., Woodinville, Wash.). Sample residual and Mahalanobis distance were used for outlier diagnostics. The scores plot was used for visualization of clustering among samples (sample patterns, groupings or outliers).

Coomans' plots were applied (FIG. 4) to assess the classification performance of the SIMCA model by predicting class membership in terms of distance from the boundaries of the prediction model. In a Coomans' plot, the two axes represent the distance of each sample from a specific class (e.g., IC or healthy), so that each class model is drawn as a rectangle corresponding to the critical distance (p=0.05) from the class. Any sample having a distance from the corresponding class rectangle greater than the critical distance is identified as being outside the class model and, as a consequence, rejected as an outlier from the specific class (graphically, it is plotted outside the rectangle defining the class model). Samples plotted onto the lower left square of the diagram are assigned to both classes.

Figure 4:
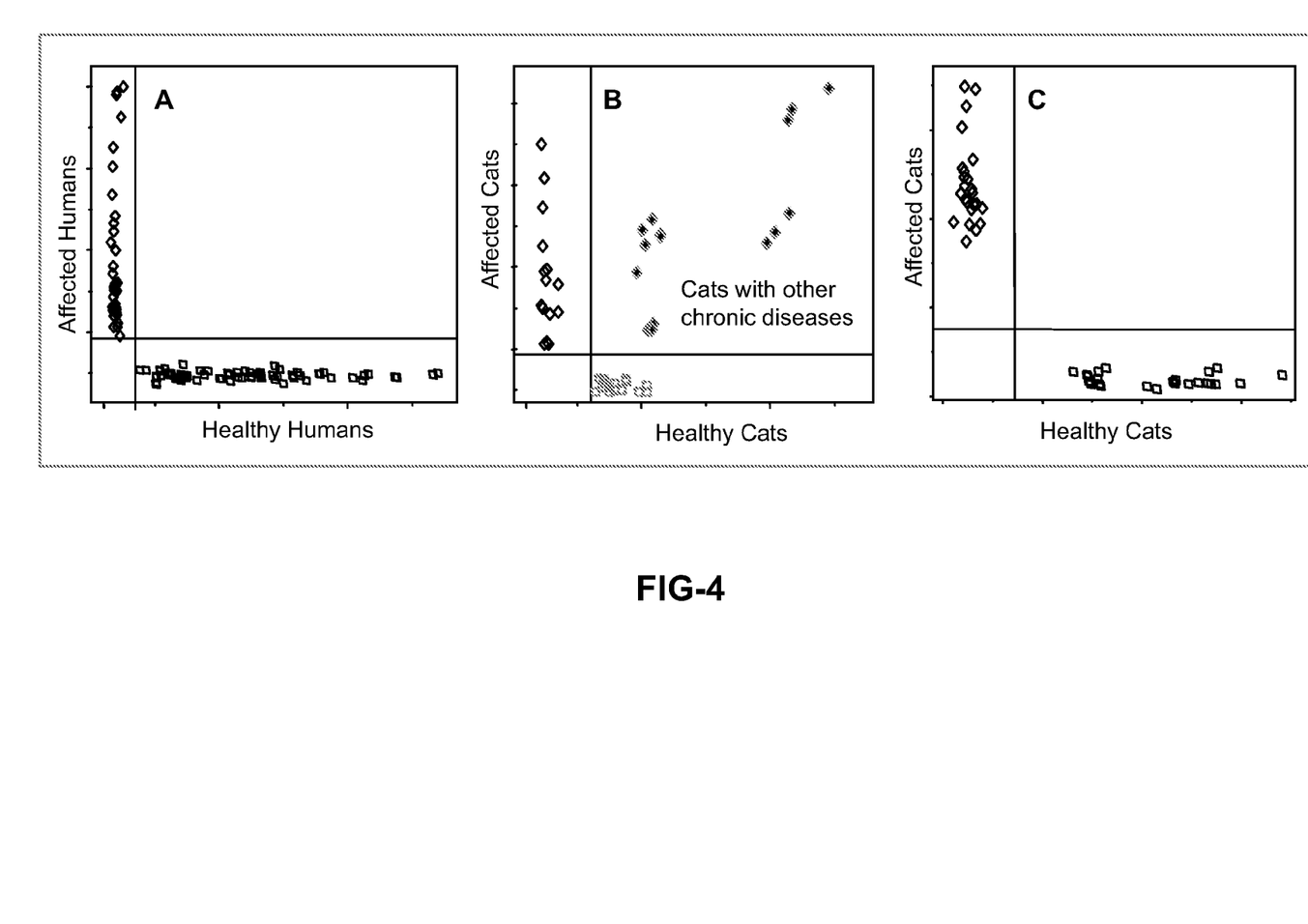
FIG. 4 shows Coomans plots of IR microspectroscopy spectra. The vertical and horizontal lines represent the 0.05 confidence limits between groups. (A) human serum samples for IC/CPPS-IIA diagnosis, demonstrating that the healthy and affected classes of test samples did not share common multivariate space and (B) domestic cat serum for FIC, healthy and subjects with chronic disorders other than FIC.

Initial IR spectra from feline (FSF) and human serum films (HSF) showed similar spectral profiles (FIG. 1) with no observable differences between spectra from (F)IC affected and healthy subjects. However, SIMCA analysis of the transformed (second derivative) IR spectra revealed specific bands that permitted the classification of samples according to presence or absence of (F)IC (FIG. 4A), with interclass distances of 4.1 and 7.9 for cats and humans (see Table 1), respectively, providing evidence of chemical differences between the serum of healthy and (F)IC afflicted subjects. Spectra from cats suffering disorders other than (F)IC differed from the healthy control and (F)IC groups (FIG. 4B).

TABLE 1

Interclass distances in 2-class SIMCA models using type α DSF.

| Human Model | | Cat Model | |
|---|---|---|---|
| Healthy (10) | | Healthy (21) | |
| Sick (35) | 7.9 | Sick (33) | 4.1 |

\* Number of factors between parentheses
\*\* F-Test confidence level: 95%

The fundamental role of interclass distance in multivariate classification follows from the assumption that proximity in multivariate space is indicative of similarity between samples. Samples that are nearby in the multivariate space are considered to have similar characteristics, whereas large separation suggests different characteristics. In general, class distances greater than 3 suggest well separated classes.

The ability to classify the subjects into these two groups denotes spectral differences between the two classes, and provides evidence of chemical differences between the serum of healthy and IC-afflicted subjects. Remarkably, these chemical differences could be detected in films containing all serum constituents in both human and cat samples (DSF type α).

The classification of specimens as (F)IC or healthy using type α DSF produced complex SIMCA models (large number of factors) presumably due to the presence of many other compounds present in the samples not related with the disease (hormones, lipids, etc). To decrease the complexity of the models and increase the prediction capabilities various embodiments employ two strategies by: (a) introducing more information (classes) in the models (subject gender) and (b) extracting serum constituents that may not be related with the disease (type β DSF).

Regarding (a), the inclusion of gender in the classification models (4-class models: healthy-male, healthy-female, sick-male, and sick-female) produced less complex models with fewer numbers of factors in each class and larger interclass distances (Table 2).

TABLE 2

Interclass distances in 4-class SIMCA models using type DSF.

| | Healthy Male | IC Male | Healthy Female |
|---|---|---|---|
| Human | | | |
| Healthy Male (10) | — | — | — |
| IC Male (11) | 19.5 | — | — |
| Healthy Female (9) | 11.6 | 6.2 | — |
| IC Female (14) | 12.6 | 3.9 | 7.1 |
| Cat | | | |
| Healthy Male (8) | — | — | — |
| IC Male (15) | 7.1 | — | — |
| Healthy Female (12) | 16.8 | 5.7 | — |
| IC Female (14) | 17.1 | 5.8 | 4.9 |

\* Number of factors between parentheses
\*\* F-Test confidence level: 95%

These results corroborate that IR spectra contained information about other characteristics of the subjects that could be included in the models to simplify and increase their prediction capabilities. Besides gender, other characteristics, such as age, diet, intercurrent disease, that might influence serum composition could be introduced as factors to make SIMCA models more robust.

Regarding (b), SIMCA models generated using the IR spectra from membrane-filtered cat serum solutions (FIG. 4C) resulted in greater interclass distances between FIC and healthy subjects, from 4.1 to 5.9, and again correctly classified each one of the spectra.

Example 4

Diagnosis Capabilities

Prediction Models.

The diagnostic capabilities of the method were evaluated using type α DSF: 4 spectra from every sample were put together to create SIMCA prediction models for cats (136 spectra) and for humans (116 spectra). The other 2 spectra from every sample (68 from cats and 58 from humans) were used as blinds to evaluate the models as percentage of blind spectra correctly classified. To assess the variability introduced by film preparation new DSF were made from random samples collected from 10 cats. At least 2 of the 3 spectra from every new film had to be recognized by the SIMCA models to consider the film correctly identified. Whenever spectra from the same film had contradictory identifications, the results were reported as misidentified.

SIMCA prediction models based just on the condition of the subjects (2-class) were able to identify 96% ($55/57$) and 93% ($63/68$) of human and cat blind spectra respectively (Table 3). 4-class prediction models performed better in the identification of blind spectra, correctly identifying 98% ($56/57$) of human and 97% ($66/68$) of cat specimens.

TABLE 3

Identification of blind spectra using SIMCA prediction models

|  | Human Models | | Feline Models | |
|---|---|---|---|---|
| SIMCA Classes | Healthy or Sick | Healthy-Male, Sick-Male Healthy-Female, Sick-Female | Healthy or Sick | Healthy-Male, Sick-Male Healthy-Female, Sick-Female |
| Number of specimens | 29 | 29 | 34 | 34 |
| Total collected spectra | 174 | 174 | 204 | 204 |
| Spectra used for SIMCA models | 116 | 116 | 136 | 136 |
| Spectra used as blinds* | 57 | 57 | 68 | 68 |
| Correcly classify | 55 | 56 | 63 | 66 |
| Mispredicted | 0 | 0 | 0 | 0 |
| Not-recognized | 2 | 1 | 5 | 2 |
| Correcly diagnose specimes** | 100% | 100% | 100% | 100% |

*One HDSF spectrum considered anomalous was removed from the study.
**At least 1 of the 2 blind spectra from each specimen was recognized. There were no mispredictions.

These results support the feasibility of detecting specific information in the DSF infrared spectra able to determine if a subject is afflicted with (F)IC or not. 100% of the subjects were correctly diagnosed by predicting their condition using the blind spectra. For this evaluation, specimens were considered to be correctly diagnosed if at least 1 of the 2 blind spectra was correctly classified, and there was no contradiction between the two.

The spectra used as blinds in the previously mentioned evaluation came from the same group of DSF produced to make the SIMCA models and therefore did not consider the variability introduced by the dried film preparation procedure. To further evaluate the method we tested the models with IR spectra from a new set of DSF (Table 4). Sixteen of 20 new dried films prepared to evaluate the variability produced by the DSF preparation step were correctly identified (at least 2 out of 3 spectra had to be identified per film). This shows that film preparation, indeed, increased the variability and reduced the prediction capabilities of the models. Yet, the spectra collected from these new dried films were enough to correctly identify the condition of all specimens involved in the test (at least 1 DSF per subject and no misidentifications).

TABLE 4

Identification of blind spectra from new CSDF.

| Specimen | Class | New films (3 spectra/ film) | Correctly identified Films* | Not-recog-nized | Wrongly identified |
|---|---|---|---|---|---|
| A | female-sick | 2 | 2 | 0 | 0 |
| B | male-sick | 2 | 2 | 0 | 0 |
| C | female-sick | 2 | 1 | 1 | 0 |
| D | female-sick | 2 | 2 | 0 | 0 |
| E | female-healthy | 2 | 1 | 1 | 0 |
| F | female-healthy | 2 | 2 | 0 | 0 |
| G | male-healthy | 2 | 2 | 0 | 0 |
| H | male-sick | 2 | 1 | 1 | 0 |
| I | female-healthy | 2 | 2 | 0 | 0 |
| J | male-heathy | 2 | 1 | 1 | 0 |
| TOTAL |  | 20 | 16 | 4 | 0 |

*At least 2 of the 3 spectra from every film had to be correctly classified for the film to be considered identified.

In a SIMCA discrimination power graph values close to 0 indicate low discrimination ability of a variable (in IR spectroscopy each wavelength is considered a variable), whereas larger values imply high discrimination power. Notably, the discrimination power analysis of the 4-class models revealed that infrared wavelengths between 1300 and 1800 cm−1 were key for the classification of human and feline subjects (FIG. 5), and suggest chemical similarities in the IC expression for both species.

Example 5

Figure 5:
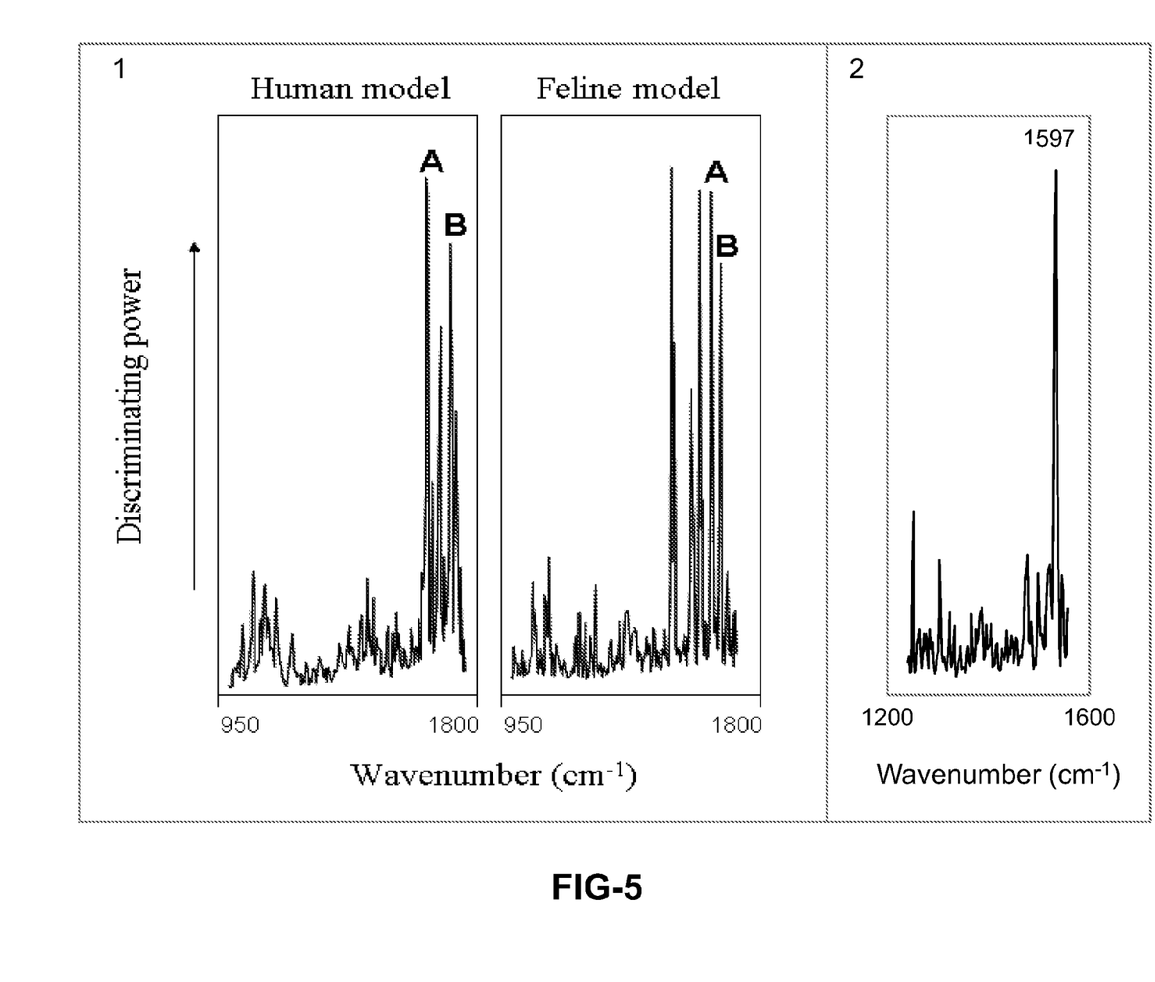
FIG. 5 shows (1) discriminating power plot of human and feline SIMCA models based on the infrared spectra of dried serum films (4-class models). The same infrared region (1500-1700 cm−1) was important for models of both species. Letters A (~1660 cm−1) and B (~1740 cm−1) denote similar bands. (2) Discriminating power plot of cat serum samples after membrane filtration (2-class model).

Quantitative Technique to Identify Compounds Responsible for the Spectral Differences The SIMCA models revealed that most of the variance between (F)IC and healthy subjects could be explained by changes in IR peaks in the 1550-1600 $cm^1$ range, suggesting chemical similarities of the biomarker in both species (FIG. 5-1). As shown in FIG. 5-2, the band at 1597 $cm^{-1}$, associated with indole ring vibrations, was one of the most important signals to discriminate healthy cats from cats with FIC, suggesting that derivatives from tryptophan may be linked to functional syndromes like (F)IC.

Based on the information provided by IRMS, we developed a liquid chromatography-mass spectrometric (LC-MS) method to measure concentrations of tryptophan and two of its metabolites, kynurenine and 5-hydroxy indole acetic acid, in cat serum.

Analytes were separated using reversed-phase liquid chromatography on a 3.5 μm Symmetry C18 column (4.6×150 mm, Waters Corp., Milford, Mass., USA). The mobile phase (0.8 ml/min) was acidified water (0.5% TFA) during the first 8 minutes; afterwards, methanol was linearly introduced from 0 to 30% in 12 minutes. Spectral information over the wavelength range of 254-700 nm was collected on a PDA detector. Mass spectrometry was conducted on a quadrupole ion-tunnel MS equipped with electrospray ionization (ESI) interface (Shimadzu, Columbia, Md.). Biomarker identification was done with authentic standards.

The 10 FIC cats examined had higher serum concentrations of tryptophan (21% higher; % RSD: 23% (affected), 19% (healthy); p=0.07) and kynurenine (23% higher; % RSD: 27% (affected), 23% (healthy); p=0.09) than did the 10 healthy cats, whereas concentrations of 5-hydroxy indole acetic acid were not different (p=0.45). Interestingly, sera from patients with chronic fatigue syndrome reportedly also have comparably higher concentrations of tryptophan than does sera from healthy individuals.

The following references and others cited herein but not listed here, to the extent that they provide exemplary procedural and other details supplementary to those set forth herein, are specifically incorporated herein by reference.

1. Manu P. 2000. The Pharmacotherapy of Common Functional Syndromes: evidence-based guidelines for primary care practice. Haworth press. England
2. Metts, J. F. 2001. Interstitial Cystitis: Urgency and Frequency Syndrome. Am Fam Physician 64:1199-1206.
3. Ratner V., Taylor N., Wein A. J., Hanno P. J. 1999. Epidemiology of interstitial cystitis: a population based study. J Urol 162:500.
4. Curhan G. C., Speizer F. E., Hunter D. J., Curhan S. G., Stampfer M. J. 1999. Epidemiology of interstitial cystitis: a population based study. J Urol 161:549-52.
5. Buffington CAT. 2004. Comorbidity of Interstitial Cystitis with other Unexplained Clinical Conditions. Journal of Urology. 172:1242-1248.
6. The Urology Channel: http://www.urologychannel.com/interstitialcvstitis/index.shtml Accessed on 29 Mar. 29, 2009.
7. Keay S., Takeda M., Tamaki M. and Hanno P. 2003. Current and future directions in diagnostic markers in interstitial cystitis. Intl J Urol 10: S27-S30.
8. Buffington, C. A. T., Chew, D. J., Woodworth, B. E. 1999. Feline Interstitial Cystitis. J Am Vet Med Assn, 215:682.
9. Buffington, C. A. T., Chew, D. J., Woodworth, B. E. 1997. Idiopathic Cystitis in Cats: an Animal Model of Interstitial Cystitis. In: Interstitial Cystitis. Edited by G. R. Sant. Philadelphia: Lippincott-Raven, pp. 25-31.
10. Clauw D J, Chrousos G P. 1997. Chronic pain and fatigue syndromes: Overlapping clinical and neuroendocrine features and potential pathogenic mechanisms. Neuroimmunomodulation. 4(3):134-153.
11. Buffington CAT. 2004. Comorbidity of Interstitial Cystitis with other Unexplained Clinical Conditions. Journal of Urology. 172:1242-1248.
12. Nigro D A, Wein A J. Interstitial Cystitis: Clinical and Endoscopic Features. In: Sant G R, ed. Interstitial Cystitis. Philadelphia: Lippincott-Raven, 1997:137-142.
13. Gunnar M R, Fisher P A. Bringing basic research on early experience and stress neurobiology to bear on preventive interventions for neglected and maltreated children. *Development and Psychopathology* 2006; 18:651-677.
14. Aaron L A, Burke M M, Buchwald D. Overlapping conditions among patients with chronic fatigue syndrome, fibromyalgia, and temporomandibular disorder. *Archives of Internal Medicine* 2000; 160:221-227.
15. Aaron L A, Herrell R, Ashton S, Belcourt M, Schmaling K, Goldberg J, Buchwald D. Comorbid clinical conditions in chronic fatigue—A co-twin control study. *Journal of General Internal Medicine* 2001; 16:24-31.
16. Clemens J Q, Brown S O, Kozloff L, Calhoun E A. Predictors of symptom severity in patients with chronic prostatitis and interstitial cystitis. *J Urol* 2006; 175:963-6; discussion 967.
17. Westropp J L, Buffington CAT. 2002. In Vivo Models of Interstitial Cystitis. The Journal of Urology. 167(2):694-702.
18. Petrich, W. 2001. Mid-infrared and Raman spectroscopy for medical diagnostics. Appl. Spectrosc. Rev. 36: 181-237.
19. Naumann, D. 2001. FT-infrared and FT-Raman spectroscopy in biomedical research. Applied Spectroscopy Reviews 36: 239-298.
20. Ellis, D., Harrigan, G. G. & Goodacre, R. 2003. Metabolic fingerprinting with Fouriertransform infrared spectroscopy. In: Metabolic Profiling: Its Role in Biomarker Discovery and Gene function Analysis (Harrigan, G. G. & Goodacre, R., eds.). Kluwer Academic Publishers, Dordrecht.
21. Fabian H., Ngo Thi N. A., Eiden M., Lasch P., Schmitt J., Naumann D. 2006. Diagnosing benign and malignant lesions in breast tissue sections by using IR-Microspectroscopy. Biochim Biophys Acta 1758:874-882.
22. Shaw R. A. and Mantsch H. H. 2001. Infrared Spectroscopy in Clinical and Diagnostic Analysis. In Encyclopedia of Analytical Chemistry. Edited by Robert A. Meyers. John Wiley & Sons Ltd, Chichester.
23. Naumann, D. 2000. FT-Infrared and FT-Raman spectroscopy in biomedical research. In Infrared and Raman spectroscopy of biological materials. Edited by Hans-Irich Gremlich and Bing Yang. Marcel Dekker, New York.
24. Ellis, D. I. and Goodacre, R. 2006. Metabolic fingerprinting in disease diagnosis: biomedical applications of infrared and Raman spectroscopy. The Analyst 131:875-885.
25. Kvalheim O. M., Karstang T. V. SIMCA—Classification by Means of Disjoint Cross Validated Principal Components Models. Multivariate pattern recognition in chemometrics, Edited by R. Brereton. Elsevier, The Netherlands, 1992.
26. Tirumalai R, Chan C, Prieto A, Issaq H, Conrads T, Veenstra R. 2003. Characterization of the Low Molecular Weight Human Serum Proteome. *Molecular & Cellular Proteomics* 2.10.
27. Merrell K, Southwick K, Graves S, Esplin M, Lewis N, Thulina C. 2004. Analysis of Low-Abundance, Low-Molecular-Weight Serum Proteins Using Mass Spectrometry. Journal of Biochemical Techniques, Vol (15), 4.
28. D. Coomans, I. Braeckaert, M. P. Derde, A. Tassin, D. L. Massart, S. Wold, 1984. Use of a microcomputer for the definition of multivariate confidence regions in medical diagnosis based on clinical laboratory profiles. Comput. Biomed. Res. 17, 1-14.
29. Lambert J, Shurvell H, Lightner D, Cooks G. 1998. Organic Structural Spectroscopy. Prentice Hall Upper Saddle River, N.J.
30. Dantzer R, O'Connor J C, Freund G G, Johnson R W, Kelley K W. From inflammation to sickness and depression: when the immune system subjugates the brain. *Nat Rev Neurosci* 2008; 9:46-56.
31. Hsieh T, Yu K, Lin S. 2007, Possible application of Raman microspectroscopy to verify the interstitial cystitis diagnosis after potassium sensitivity test: phenilalanine or tryptophan as a biomarker, *Disease Marker* (23).

Unless otherwise defined, all technical and scientific terms used herein have the same meaning as commonly understood by one of ordinary skill in the art to which this invention pertains. Although methods and materials similar or equivalent to those described herein can be used in the practice or testing of the exemplary embodiments, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Having shown and described embodiments of the invention, those skilled in the art will realize that many variations and modifications may be made to affect the described invention and still be within the scope of the claimed invention. Thus, many of the elements indicated above may be altered or replaced by different elements which will provide the same result and fall within the spirit of the claimed invention. It is the intention, therefore, to limit the invention only as indicated by the scope of the claims.

What is claimed is:

1. A method for rapidly diagnosing a disease condition, comprising:
   receiving a fluid biomedical specimen from a test subject; separating the specimen to obtain a desired fraction;
   depositing an aliquot of the desired fraction onto a slide; drying the aliquot;
   collecting infrared spectral data from the aliquot;
   identifying at least three different spectra collection regions; and
   identifying a test subject's condition by analyzing the infrared spectral data using multivariate classification models.

2. The method of claim 1, further comprising the step of: developing multivariate classification models using previously provided spectra corresponding to reference films of afflicted subjects and non-afflicted subjects.

3. The method of claim 1, wherein the drying step further comprises the step of forming a dried film on the slide; and the collecting step comprises obtaining infrared spectral data from at least two regions of the dried film.

4. The method of claim 3, further comprising the step of: diluting the specimen to form a specimen-water solution prior to the depositing step.

5. The method of claim 4, wherein: the specimen-water solution contains at least one part water for each part fluid specimen.

6. The method of claim 1, wherein: the separating step includes the step of filtering the specimen with a membrane.

7. The method of claim 1, wherein: the separating step includes the step of ultrafiltering the specimen with a molecular weight cut-off membrane of a predetermined stringency.

8. The method of claim 1, wherein: the separating step includes the step of centrifuging the specimen using a centrifugal filter device.

9. The method of claim 1, wherein: the spectra collection regions are substantially equidistant from the center of the dried film.

10. The method of claim 1, wherein: the infrared spectral data in the collecting step is obtained via an attenuated total reflectance FT-IR method.

11. The method of claim 1, wherein the spectral data includes information for wavelengths between 1300 and 1800 cm.sup.−1.

12. A method for the rapid diagnoses of interstitial cystitis and related syndromes, comprising:
   receiving a sample from a patient; separating the sample to obtain a desired fraction;
   depositing an aliquot of the fraction onto a microscope slide;
   drying the aliquot to form a dried film on the slide;
   collecting infrared spectral data from the dried film;
   identifying at least three different spectra collection regions; and
   diagnosing interstitial cystitis or a related syndrome by analyzing the spectral data against multivariate classification models developed with the spectra of reference films from afflicted and non-afflicted individuals.

13. The method of claim 12, further comprising the step of: diluting the sample to form a sample-water solution prior to the separating step.

14. The method of claim 12, wherein the spectral data includes information from wavelengths between 1300 and 1800 cm.sup.−1.

15. The method of claim 12, wherein: the separating step is performed using a centrifugal filter device.

16. The method of claim 12, wherein: the aliquot comprises about 0.01 .mu.l to 1 .mu.l of the desired fraction.

17. The method of claim 12, wherein: the drying step comprises the application of a vacuum.

* * * * *